US012593963B2

(12) United States Patent
Kalim et al.

(10) Patent No.: US 12,593,963 B2
(45) Date of Patent: Apr. 7, 2026

(54) IMAGING SYSTEM AND LAPROSCOPE FOR IMAGING AN OBJECT

(71) Applicant: JOSHI INNOVATIONS GMBH, Wurmlingen (DE)

(72) Inventors: Faisal Kalim, Munich (DE); Subhamoy Mandal, Heidelberg (DE); Shirish Joshi, Wurmlingen (DE)

(73) Assignee: Joshi Innovations GmbH, Wurmlingen (DE)

( * ) Notice: Subject to any disclaimer, the term of this patent is extended or adjusted under 35 U.S.C. 154(b) by 243 days.

(21) Appl. No.: 18/253,495

(22) PCT Filed: Nov. 11, 2021

(86) PCT No.: PCT/EP2021/081374
§ 371 (c)(1),
(2) Date: May 18, 2023

(87) PCT Pub. No.: WO2022/101338
PCT Pub. Date: May 19, 2022

(65) Prior Publication Data
US 2024/0366072 A1      Nov. 7, 2024

(30) Foreign Application Priority Data

Nov. 13, 2020 (EP) .................................... 20207498

(51) Int. Cl.
| | | |
|---|---|---|
| *A61B 1/00* | (2006.01) | |
| *A61B 1/04* | (2006.01) | |
| *A61B 1/313* | (2006.01) | |

(52) U.S. Cl.
CPC .... *A61B 1/00193* (2013.01); *A61B 1/000094* (2022.02); *A61B 1/00165* (2013.01);
(Continued)

(58) Field of Classification Search
CPC .......... A61B 1/00193; A61B 1/000094; A61B 1/00165; A61B 1/00183; A61B 1/00188; A61B 1/042; A61B 1/3132
See application file for complete search history.

(56) References Cited

U.S. PATENT DOCUMENTS

| | | | | |
|---|---|---|---|---|
| 2010/0245552 A1* | 9/2010 | Higuchi | ................. | A61B 1/043 |
| | | | | 348/E7.085 |
| 2013/0038689 A1 | 2/2013 | McDowall | | |
| 2016/0278678 A1 | 9/2016 | Valdes et al. | | |

FOREIGN PATENT DOCUMENTS

| | | |
|---|---|---|
| CN | 102598674 A | 7/2012 |
| CN | 103417176 A | 12/2013 |

(Continued)

OTHER PUBLICATIONS

International Search Report & Written Opinion for Application No. PCT/EP2021/081374; mailed Feb. 2, 2022; 12 pp.

*Primary Examiner* — Timothy J Neal
(74) *Attorney, Agent, or Firm* — Bodman PLC

(57) ABSTRACT

An imaging system (1) is provided, comprising: an optical channel (2) configured to transfer light, a first sensor (10) configured to generate first image data by imaging an object (3) along a first optical path (11), and a second sensor (20) configured to generate second image data by imaging the object (3) along a second optical path (21). The first sensor (10) and the second sensor (20) are focus shifted. Further, the first optical path (11) and the second optical path (21) are guided at least partly through the optical channel (3).

14 Claims, 4 Drawing Sheets

Figure 1:
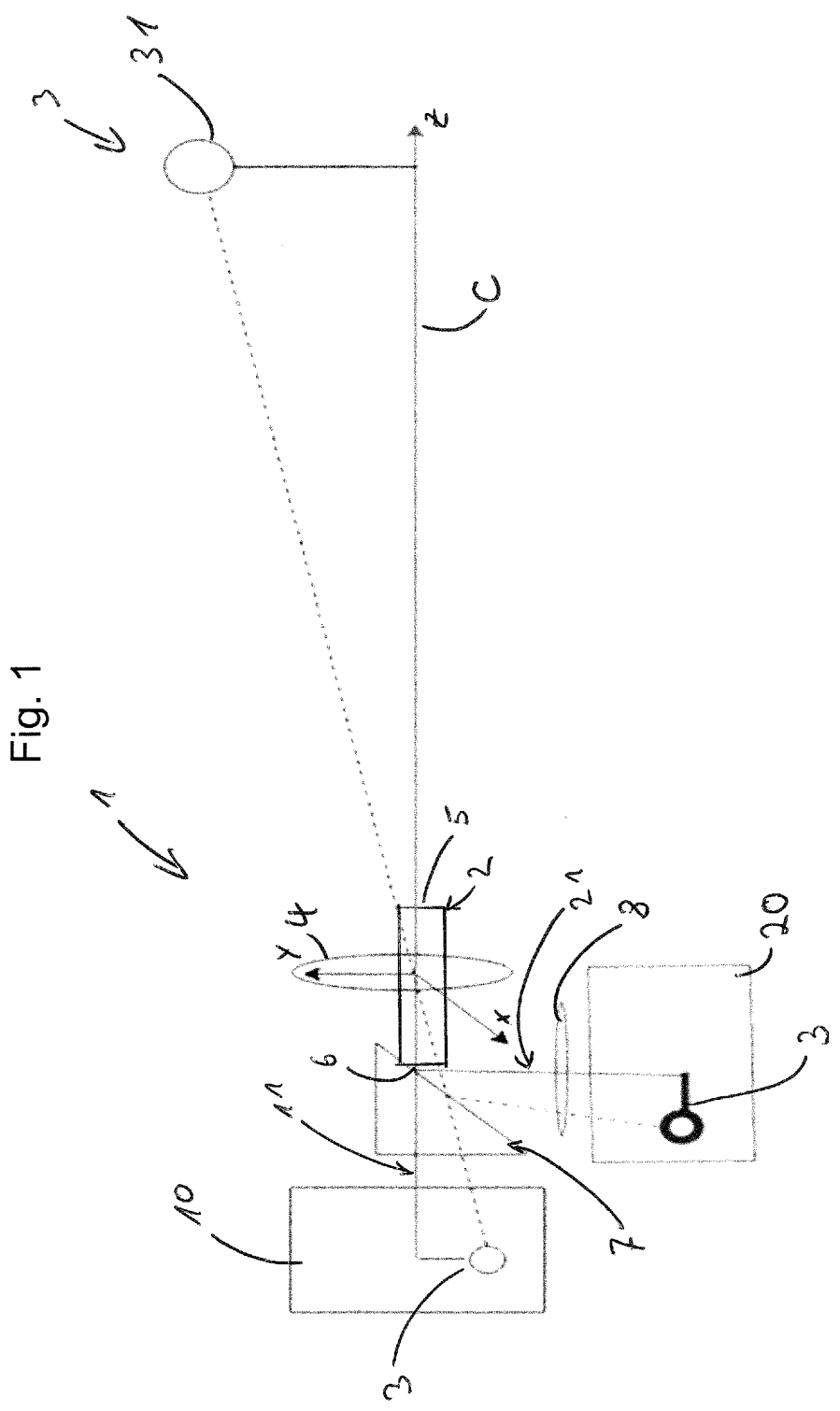

(52) U.S. Cl.
CPC ...... *A61B 1/00183* (2013.01); *A61B 1/00188* (2013.01); *A61B 1/042* (2013.01); *A61B 1/3132* (2013.01)

(56) References Cited

FOREIGN PATENT DOCUMENTS

| | | | |
|---|---|---|---|
| CN | 106236006 | B | 11/2017 |
| CN | 109259717 | A | 1/2019 |
| JP | H07236610 | A | 9/1995 |
| JP | 2000513978 | A | 10/2000 |
| JP | 2013244104 | A | 12/2013 |
| JP | 2014524290 | A | 9/2014 |
| JP | 7236610 | B2 | 3/2023 |
| WO | 2020042796 | A1 | 5/2020 |

\* cited by examiner

IMAGING SYSTEM AND LAPROSCOPE FOR IMAGING AN OBJECT

The present invention relates to an imaging system, a laparoscope and a method for imaging an object.

Imaging systems may be used to acquire images of an object to be imaged. The imaging system may be provided in a laparoscope or endoscope that is used as a videoscope, often also called videoscope or video probe. In such laparoscopes an image sensor is attached to the objective of the laparoscope and configured to acquire an image of the object under examination; which may be an organ inside the body or another kind of object that is difficult to access, such as the inside of a machine. Therefore, Laparoscopes are slim devices with little space inside. Hence, it is difficult to include an imaging system inside the laparoscope that may be used to acquire detailed images of an object to be imaged.

EP 1691667 A1 discloses a stereoscopic laparoscope apparatus comprising a laparoscope, a computer adapted to convert and store image information of the patient's affected part from the laparoscope, and a monitor used to output the image information. The laparoscope comprises a supporting unit including a manipulator, and a pair of parallel left and right supporting rods, a flexible tube unit including a pair of left and right flexible tubes, which are adapted to be spaced apart from each other within a predetermined angular range, and a binocular camera assembly including a pair of left and right cameras installed at the tip end of the flexible tube unit so that they take images of the affected part in the abdominal cavity under operation of the manipulator. With such configuration, the image information of the patient's affected part can be processed into stereoscopic photographs, resulting in precise diagnosis and laparoscopic surgery.

However, the stereoscopic technique is a technique for creating only an illusion of depth in a photograph by means of stereopsis for binocular vision. Nevertheless, for a detailed analysis of the object to be imaged it would be desirable to provide real depth information.

Therefore, it is an object of an embodiment of the present invention to provide an imaging system, a laparoscope and a method for imaging an object that may acquire images useable for determining real depth information of an object.

The object is solved by an imaging system including the features of claim 1, a laparoscope including the features of claim 12 and a method for imaging an object including the features of claim 13.

According to an aspect of the present invention an imaging system is provided, comprising: an optical channel configured to transfer light, a first sensor configured to generate first image data by imaging an object along a first optical path, and a second sensor configured to generate second image data by imaging the object along a second optical path, wherein the first sensor and the second sensor are focus shifted, and wherein the first optical path and the second optical path are guided at least partly through the optical channel.

The imaging system may be an optical imaging system and may be used to create image data of the object using the first sensor and the second sensor. That is, the first image data and the second image data may image the same part of the object from the same viewing angle. This is achieved by providing a dual sensor imaging system that may generate first and second image data in quick succession or simultaneously. The imaging data preferably comprises a sequence of images, e.g. a video stream. Further, since the first optical path and the second optical path are guided through the same optical channel, the direction in which the object is imaged (i.e. the viewing angle) of the first sensor and the second sensor is the same. As a result, the first image data and the second image data are automatically registered to each other so as to perfectly overlap with one another without the need to execute any additional alignment or registration process. Since the first sensor and the second sensor are focus shifted, the first image data has a different focus point (i.e. a point at which the object is sharply depicted by the image data) as compared to the second image data. That is, the first sensor may be focused to a point having a first distance d1 from a distal end of the optical channel and the second sensor may be focused to a further point having a second distance d2 from the distal end of the optical channel. The difference of the first distance d1 and of the second distance d2 may be the focus shift of the two sensors. The focus shift may be determined by the hardware of the imaging system. In more detail, the focus shift may be provided by the arrangement of the sensors within the imaging system and/or by an optical systems within the imaging system. Accordingly, the focal length and/or the optical paths may be shortened or extended by a specific arrangement of the sensors or by the optical system (to be explained in more detail below).

The imaging system may be provided within a laparoscope which may be used to provide inevitable information for diagnosing and treatment related to internal organs of the human or animal body. In addition, the laparoscope may be used in maintenance of large machinery, e.g. to check whether gears that are difficult to access have to be exchanged or not, without demounting the whole machinery. The sensors of the imaging system may be accommodated within a camera head of the laparoscope such that a camera head may be provided having a dual sensor, wherein each sensor has its own focus. In other words, the sensors may be housed solely in the camera head so that there is no sensor in the shaft. Accordingly, the shaft may be made slim so that it may be operated without problems in narrow cavities, for example. Therefore, the sensors may be outside the cavity to be inspected during operation. Among other things, this leads to the fact that the weight distribution of the endoscope may be advantageously modified so that the shaft has a relatively low weight compared to the camera head. Since the endoscope is held at or near the camera head by the user or robot, the operation of the endoscope may be further simplified. That is, each sensor may have its own focus point such that the sensors are focus shifted with respect to each other. For example, each sensor may have its own focal length. That is, the focal length of the sensors may be different. Further, the laparoscope may have a shaft protruding from the camera head, that may be brought in the vicinity of the object to be imaged. That is, the shaft may be at least partly inserted into a human body or into a narrow cavity, for example, and wherein the shaft may comprise the optical channel. The shaft may be connected to the camera head at a proximal end thereof. The camera head may be removed from the shaft. In other words, the sensors may be separated from the shaft. Accordingly, the sensors may be easily replaced, changed, repaired, maintained, etc. without having to disassemble the shaft itself. This means that the shaft may continue to be used, while only the camera head may be replaced. The distal end of the shaft may be facing the object to be imaged. The shaft as well as the optical channel may be configured to be at least partly flexible. Furthermore, the shaft may be controllably moveable (e.g. controllably bendable so as to redirect the distal end of the shaft). As a result, the laparoscope may be adapted to any environment in which it is to be used and may reach regions located behind other objects. Within the shaft the optical channel may be provided (e.g. in the form of a wave guide) which is configured to guide the first optical path and the second optical path from the proximal end of the shaft to the distal end of the shaft independent of the flexion of the shaft. In addition, at the distal end and/or at the proximal end of the shaft, an optical device (e.g. a lens or an array of lenses) may be provided, respectively, in order to appropriately guide the first optical path and the second optical path into the wave guide and out of the wave guide.

The shifted focus of the first sensor and the second sensor (for example a different focal length of each sensor) may be realized by providing at least one additional lens in at least one of the optical paths of each sensor. However, only one additional lens may be provided in at least one optical path. Moreover, there may be provided further lenses or an optical system to appropriately direct light from the object to the sensors. Using the imaging system according to one embodiment of the present invention provides first and second image data that overlap perfectly with one another and that may be directly further processed without the need for any additional registration process. For example, perfectly overlapping images each having a different focus (e.g. focal point) may be used to determine depth information of the object (further details will follow below).

The optical channel may be an elongated body. Further, the optical channel may be hollow or made of a transparent material. The optical channel may have a proximal end facing the first sensor and the second sensor and a distal end facing the object to be imaged. The distal end may protrude from the imaging system and may be the outlet port of the first optical path and the second optical path. Therefore, the first optical path and second optical path are aligned to each other at the distal end such that the viewing angle of the first sensor and of the second sensor are the same. The optical channel may be configured such that the optical paths exiting the optical channel at the distal end extend in a divergent manner, preferably having an extension angle of 30° to 90°, preferably of 50° to 70° (i.e. the optical paths may become a cone shape once they have exited the optical channel so as to capture a larger scene). For example, the optical channel may be made of an optical fiber. In addition, the optical channel may be at least partly flexible such that it may guide light even if the optical channel describes a curve. Preferably, the optical channel is flexible in accordance to the shaft of a laparoscope in which it is provided. Therefore, objects positioned behind an obstacle may be easily imaged by routing the shaft around the obstacle. The imaging system may have only one optical channel. Accordingly, the imaging system may be compact such that only less space is necessary to operate the imaging system. On the other hand, stereoscopic imaging systems may have two or more optical channels due to inherent system requirements and therefore may need more space for operation.

The first and the second sensor may be photo sensors also referred to as image sensors or sensor chips, preferably complementary metal-oxide-semiconductor (CMOS) sensors, also known as complementary-symmetry metal-oxide-semiconductor (COS-MOS) sensors. Further, the first and the second sensor may be charge-coupled device (CCD) sensors. The first sensor and the second sensor may be the same kind of sensors. Alternatively, the first sensor may be a different sensor as compared to the second sensor. By providing different kind of sensors different image quality and/or different image information may be acquired. For example, a low-resolution image data may be used to provide rough information of the object, whereas a high-resolution image may be used in further processing and for detailed information. Preferably, the minimum resolution of at least one sensor is 1080×1920 pixels. Preferably, each sensor has the same resolution. Hereinafter, it is referred to the first sensor and to the second sensor, however, the imaging system may have more than two sensors, each sensor having its own optical path. That is, if three sensors are provided there are also three optical paths provided and so on. For example, the imaging system may have three, four, five or more sensors. In this case, each optical path of each sensor is guided at least partly through the same optical channel. The use of more sensors is specifically useful if the object to be imaged has a large spatial extension or if very detailed information of the object to be imaged are to be obtained. Further, each sensor may have its own shutter configured to control the amount of light that is applied onto the sensor. As a result, by adjusting the shutter speed, the sensor may be adapted to different light conditions. Alternatively, the sensor may acquire a continuous video stream of image data.

In case a CMOS sensor is used, the image data may be a voltage signal that is outputted by the sensor. Preferably, each pixel of the sensor may have a specific voltage signal. That is, CMOS sensor may output a digital signal. In case the CCD sensor is used, the image data may be a charge signal. The voltage signal is less prone to be deteriorated by electromagnetic fields and thus a CMOS sensor is preferably used as the sensor of the imaging system.

The image data may be an output of the sensors. Moreover, the image data may include brightness information for one or more color channels. A color channel may represent a specific light spectrum. For example, the image data may comprise information for the green color channel, the RGB color channel and/or the NIR (near-infrared) color channel. The RGB color channel is considered as including the green color channel, the red color channel and the blue color channel. Further, each sensor may provide image data including information of different color channels. That is, the first sensor may provide first image data including information of the green channel, whereas the second sensor may provide second image data including information of the NIR-channel. In addition, further combinations of different color channels of each sensor are possible such as NIR-NIR, RGB-RGB, green-green, NIR-RGB, green-NIR, green-RGB. Wherein each color channel may be defined by a different band of wavelengths. For further processing of the image data, the imaging system may be connected or connectable to a processing unit (e.g. a computer) or may have a control unit. The control unit may be configured to further process the image data. For example, the control unit may determine the information contained within the image data, e.g. a histogram showing the brightness distribution. In addition, the image data may comprise an image or photograph depicting the object. In order to cope with bad light conditions, the imaging system may have a light source configured to light the object to be imaged. In more detail, the light source may be coupled with an additional wave guide that is configured to guide the light of the light source within or parallel to the optical channel to the object to be imaged.

The optical paths are the paths that the rays of light take from the object to the sensors. That is, light may be reflected by the object to be imaged, introduced into the optical channel, guided through the optical channel, outputted by the optical channel and captured by the first and second sensors. The optical paths may be defined by rays of light that are received by the respective sensor. In other words, the length of the optical path may be measured from the sensor to the object to be imaged. In addition, within each optical path there may be provided lenses or arrays of lenses configured to appropriately guide the rays of light from the object to each of the sensors. Further, the imaging system may include at least one prism configured to split the first optical path and/or the second optical path. Preferably, the prism is configured as a beam splitter prism. The prism may be configured to filter a specific wavelength, i.e. to transfer only a specific wavelength of the light. Hence, the wavelength that is transmitted to the sensors may be pre-determined. For example, only the wavelength corresponding to the green channel may be transmitted by the prism. Further, the prism may also increase the length of one of the optical paths with respect to the other optical path. Accordingly, by the prism having several tasks, the imaging system may be realized with a minimum of components. In addition, the imaging system may include at least one aperture in the optical path or optical channel configured to control the aperture of the imaging system. That is, the wider the aperture is open, the shallower the depth of field of the image and vice versa. Generally, if the aperture is wide open, the image data has a better quality and includes more information. Therefore, it is preferred to adjust the aperture such that it has the maximum opening. As a result, the field of depth may relatively narrow. Further, the imaging system may have one aperture for each optical path.

The shifted focus of the first sensor and the second sensor may be provided by providing different focal lengths for each sensor. The focal length of the first sensor and the second sensor may be a distance from a main axis of an optical lens provided within the imaging system to the focus point along the respective optical path. The optical lens may be configured to project an image onto the sensor. Each sensor may be assigned to a separate lens. That is, in case there are two sensors, the imaging system may have two optical lenses. Further, the focal length may be a measure of how strongly the imaging system converges or diverges light. A positive focal length indicates that the system converges light, while a negative focal length indicates that the system diverges light. A system with a shorter focal length bends the rays more sharply, bringing them to a focus in a shorter distance or diverging them more quickly. For example, the ratio of the focus length of the first sensor and the second sensor may be in a range from 0.1 to 1, preferably in a range from 0.3 to 0.7. In this range the best imaging of the object may be archived. In other words, having the above ratio, the distance between the focus point of the first sensor and the focus point of the second sensor is in an optimal range. In more detail, if the first image data and the second image data are combined or compared to each other, the above ratio ensures that no information of the object is lost due to being completely out of focus. In other words, the ratio ensures that a distance between portions of the object that are in focus is not excessively large.

According to the present invention at least two image data may be received or generated that are registered perfectly with one another without any additional registration process. That is, image data of the object generated by the at least two sensors, may have the same size, the same location and may be imaged from the same view point. Accordingly, some portions of the object may be in focus on the first image data, while some other portions of the object may be in focus on the second image data. Further, some portions of the object may be partly in focus on the first image data and partly in focus on the second image data. Consequently, by combining or comparing both image data with each other an overall image or overall data may be generated that includes more information (e.g. more details, depth information etc.) of the object as compared to a single image of the object or a stereoscopic image of the object. Said combination or comparing of the image data is facilitated because both image data are registered with one another so as to overlap perfectly. That is, it is not necessary to register the image data with one another before the image data are further processed. In other words, the first image data and the second image data may include exactly the same portion (i.e. scene) of the object. As a result, the present invention provides a highly efficient way to generate image data that overlap perfectly and that can thus be easily processed. Preferably, the focus shift of the sensors is previously (i.e. prior to the imaging of the object) determined by the imaging system. That is, the focus shift may be set by the hardware of the imaging system.

Preferably, the first optical path and the second optical path have different lengths. Accordingly, the focus point of the first sensor is located at a different location as compared to the focus point of the second sensor. Preferably, the distance between at least one sensor and the proximal end of the optical channel and/or between the sensors may be adjustable. As a result, a focus distance of each sensor may be different, that is, the distance from the respective sensor to the point of the object that is sharply depicted by the respective image data. Providing different lengths of the optical paths is a simple and robust way to realize different focus distances of the first sensor and the second sensor (i.e. the focus shift of the first sensor and second sensor). For example, the sensors may have different distances from the proximal end of the optical channel. That is, the first sensor may be arranged within the imaging system so as to be located farther away from the proximal end of the optical channel as compared to the second sensor. As a result, the same sensors and the same image settings (e.g. aperture, shutter speed etc.) may be used, while the different focus points (i.e. the focus shift of the first sensor and the second sensor) are ensured by the different locations of the sensors within the imaging system. As a result, the same components may be used for acquiring the first image data and the second image data. Thus, the imaging system may be simplified and manufacturing costs may be lowered.

Preferably the first sensor and the second sensor are further configured to image the object simultaneously. That is, the first image data and the second image data may be generated or acquired at the same time. As a result, both first image data and the second image data are registered perfectly with one another because there is no possibility that the object moves or changes its shape between the time when the first image data is acquired and when the second image data is acquired. That is, the first image data and the second image data may differ from each other only by their individual focus points (i.e. focus/blur). Therefore, the imaging system may include only one shutter used for both sensors provided within the imaging system. Hence, the system may be further simplified while at the same time a perfect overlapping of the first image data and second image data is ensured.

Preferably, the system further comprises a focus system arranged in the first optical path and/or the second optical path and configured to vary the focus of the first sensor and/or the second sensor. Accordingly, the focus (e.g. focus point or focal length) of at least one sensor may be adjusted. In other words, the distance between the focus point of the first sensor and/or the focus point of the second sensor may be changed. As a result, the imaging system may be adapted to different objects having different spatial extensions. Further, the imaging system may be adapted to different applications. For example, is case the imaging system is used during a laparoscopy (i.e. in combination with a laparoscope) the first sensor is focused at a distance of 6 cm measured from the distal end of the shaft and the second sensor may be focused at a distance of 9 cm measured from the distal end of the shaft. Therefore, the focus shift of the sensors is 3 cm. The focus shift may be positive or negative depending on the specific application. Hence the imaging system may be used in a plurality of applications and a plurality of objects may be imaged using the imaging system. For example, the focus system may be configured to adjust the focus point of at least one of the sensors such that the above defined ratio between the focus point of the first sensor and the focus point of the second sensor may be obtained.

Preferably, the system further comprises a focusing means configured to control the focus system such that the focus (e.g. the focal length) of the first sensor and/or the second sensor may be adjusted. The focusing means may be a focus ring configured to be grasped by a user's hand. Therefore, the focusing means may be exposed to the outside of the imaging system (and to the outside of the laparoscope) so as to be graspable by a user. A position (i.e. rotation) of the focus ring may depend on the distance of the object to be imaged from the sensors. The larger the distance to the object, the more the focus ring has to be rotated so as to depict at least a part of the object on one of the sensors in a sharp manner and vice versa. The focusing means may be sized such that only a few fingers (e.g. 2 fingers) of a user may be in contact therewith while the other fingers of a user's hand may hold the imaging system (i.e. laparoscope). As a result, the imaging system is favorable operatable using one hand. That is, a user does not need to operate the imaging system with both hands in order to adjust the focus and to hold the imaging system. As a result, the imaging system exhibits an improved operability.

Moreover, the focusing means may be operated automatically by the control unit. In more detail, the focusing means may be controlled by the control unit so as to adjust the focus of each sensor depending of a specific application prior to the acquisition of the image data. Alternatively or additionally, the focusing means may be controlled by the control unit so as to adjust the focus distance of each sensor in predetermined steps (i.e. increments). At each step image data may be acquired by the first sensor and the second sensor. The step size may be in a range of 0.1 mm to 5 mm, preferably in a range of 0.5 mm to 2 mm. The focusing means may be provided at the camera head of the endoscope. Accordingly, at the shaft there may be no focusing means provided. This helps to keep the weight of the shaft low. As a result, the operability of the whole endoscope may be improved. Further, during operation of the endoscope, the focusing means be be positioned outside of the cavity under inspection (e.g. the human body). Therefore, the focusing means may be easily accessible for the user or for a robot.

Preferably, the first image data and the second image data represent an identical scene e.g. exactly the same portion of the object. Depending on the focus (e.g. the focal length) of the sensors and/or on different kind of sensors used, the field of view of the first image data may be smaller than the field of view of the second image data or vice versa. In order to provide the identical field of view of the object within the first image data and the second image data, the image data that covers a larger field of view may be adjusted so as to exactly include the same field of view of the object (e.g. by cutting away a part of the image data, e.g. the outer rim). As a result, both image data may be comparable or combinable in an easy way. For example, an edge of the image data may be used as a reference point in both image data. In other words, the part of the object represented by the first image data and the second image data overlap exactly. Hence, the further processing of the image data may be further improved and simplified.

Preferably, the imaging system further includes a control unit configured to generate depth information of the object based on the first image data and the second image data. In other words, the imaging system may include a control unit for further processing the image data. The control unit may be a device similar to a computer and may be configured to receive input data, to process the input data and to output processed data. In particular, the image data (e.g. a plurality of image data) including 2D coordinates of the object may be the input data and a third coordinate (i.e. the depth information or 3D shape information) of the object may be the output data. The generation of the depth information is one example for which the plurality of image data may be used. That is, the control unit may output a depth map (e.g. 3D image data) of the object. Specifically, the depth map may be a scatter plot of points each having three coordinates describing the spatial position or coordinate of each point of the object. That is, the control unit may be configured to determine a depth map based on the first image data and the second image data.

Further, the control unit may be configured to divide the image data into segments of one or several (e.g. >9) pixels, referred to as patches. In addition, the control unit may be configured to compare a patch of the first image data with a patch of the second image data. The patches may be rectangular or quadratic patches. In particular, the control unit may be configured to determine how sharp the object is depicted in each patch (i.e. to determine a sharpness of each patch). The patches may have multiple sizes. That is, the size of the patches provided in the respective image data may vary depending on the object that is depicted by the image data and/or on the specific application (e.g. the kind of surgery). That is, in areas where a lot of texture exists, the patch size may be smaller (e.g. 5×5 pixels), whereas in areas of the image data where pixel intensities are more homogeneous, i.e. there is little texture, the pixel size may be larger (e.g. 50×50 or up to 1000 pixels). For example, a lot of texture may be in an area of the image data where a lot of edges are depicted. Accordingly, the imaging system may work in a highly efficient way, because in areas where there is a lot of texture, the patch size is small (i.e. the resolution is high) so as to obtain highly accurate information of this area, whereas in areas where there is little texture, the patch size is bigger so as to accelerate the process carried out by the control unit.

Preferably, the location of the at least one or each first patch in the first image data corresponds to the location of the at least one or each second patch in the second image data. Preferably, the at least one first patch preferably has the same size as the at least one second patch, preferably a size of 20×20 pixels. That is, the first patch has the same location within the first image data as the second patch within the second image data. In more detail, if the first image data and the second image data are registered with one another, the first patch and the second patch overlap with one another. Accordingly, for each patch a depth value (i.e. the z-coordinate) may be determined by the control unit (i.e. for each patch x, y and z coordinates in 3D space are determined). A patch may have a size of one or several pixels. However, the required computing resources are depending on the number of patches included within the image data. Therefore, preferably each patch may have a size of 20×20 pixels. Having this size, the efficiency of the system is ensured while a high accuracy of the depth map is ensured.

Further, the control unit may be configured to determine the sharpness of each patch of the first image data and each patch of the second image data. It is to be noted that several patches may have the same sharpness. The sharpness of each patch is proportional to the entropy of the respective patch. In other words, the sharpness is synonymous for the entropy. A patch of the first image data may be considered as a first patch and a patch of the second image data may be considered as the second patch. The first patch and the second patch may overlap perfectly with one another (i.e. depicting the same scene/part of the object). In other words, the first patch and the second patch (also referred to as a pair of patches) may be located at the same location within the first image data and within the second image data. As explained above the focus distance of the first sensor and of the second sensor may be previously set. Therefore, the focus distances of the first sensor and of the second sensor is known. Using the following formula the control unit may determine the depth (i.e. the z-coordinate) of the part of the object depicted by the first patch and the second patch.

$$d = \frac{(d_1 * I_1 + d_2 * I_2)}{(I_1 + I_2)}$$

wherein d is the unknown distance (i.e. depth or z-coordinate) of a part of the object depicted in the first patch and the second patch, $d_1$ is the focus distance of the first sensor, $I_1$ is the sharpness of the first patch, $d_2$ is the focus distance of the second sensor, $I_2$ is the sharpness of the second patch.

The focusing distances of the first sensor and the second sensor and the patch size has to be selected carefully so as to attain useful depth information using the above formula. Preferably, the focus distances are dependent on the specific application that is executed (e.g. the specific surgery or laparoscopy that is performed). For example, the focus distance of the first sensor may be 6 cm measured from the distal end of the shaft and the focus distance of the second sensor may be 9 cm from the distal end of the shaft. The focus distance of the first sensor may an empirical value determined from the type of surgery (e.g. for laparoscopy it may be 6 cm measured from the tip of the laparoscope (i.e. the distal end of the shaft)).

The sharpness of the image may be expressed by the information density of the image (e.g. the entropy) of the specific patch. The control unit may be configured to apply the above formula to each pair of patches (i.e. to each first patch and to each corresponding second patch) of the first image data and the second image data. As a result, a depth value for each pair of patches of the image data may be determined by the control unit. Having the depth information, the control unit may be configured to create a depth map using the depth information and the x and y coordinates of the respective pair of patches. In other words, the control unit may be configured to create a 3D model based on the x, y and z coordinates of each pair of patches.

Alternatively or additionally, the control unit may be configured to create a 3D model using the method of focus stacking. A further method that may be used to create a depth map is the so-called depth from focus/defocus. In addition, the control unit may be configured to carry out one or more of the above methods in order to create the depth information (i.e. 3D image data) based on at least two 2D image data (i.e. the first image data and the second image data). Specifically, the control unit may be configured to combine at least two methods for creating a depth map. In particular, the above formula may be applied to patches of the image data having a relatively high texture compared with other patches of the image data. In addition, the shape from lightning method may be applied to other regions of the image data having relatively poor texture compared with other regions of the image data. As a result, the performance of depth map generation may be significantly improved by applying different methods to different portions of the image data. Hence, at least one embodiment of the present invention may convert a relative difference of focus of the image data obtained by two sensors into 3D shape information. In other words, 3D coordinate of all patches within the image data may be calculated/determined by comparing the focus/blur of the respective patch (i.e. of one pixel or an array of pixels) generated by each sensor. Optionally, the control unit may be configured to further process the depth map by filtering the resulting depth map. In more detail, in order to delete erroneous depth information, the control unit may be configured to compare depth information of the depth map adjacent to each other. In case, one depth is excessively high or low (i.e. exceeding a preterminal threshold) compared to its neighbors, the control unit may be configured to delete such depth information because it is most likely that this depth information is an error. As a result, the outputted depth map by the control unit may have an increased accuracy.

Preferably, the control unit is further configured to generate the depth information by comparing the entropy of at least one first patch of the first image data and of at least one second patch of the second image data. The sharpness of the image is a synonym to the entropy. The entropy is an example of the information (i.e. a measure of the sharpness of a patch of the image data) included within the image data.

That is, the first image data and the second image data may be compared to each other on the basis of their entropy. Accordingly, the control unit may be configured to determine the entropy of the first image data and of the second image data. Specifically, the higher the entropy, the more the respective image data is in focus. Accordingly, the lower the entropy, the less the respective image data is in focus (i.e. is blurred). The entropy may be determined by the following formula:

$$H = -\sum_k p_k \log_2(p_k)$$

wherein k is the number of levels of one channel or band (e.g. the gray-channel or the green-channel under observation) and $p_k$ is the probability associated with gray level k. Further, as the band the RGB-channel and/or the NIR-channel may be used. The sharpness $I_1$ and $I_2$ used in the above formula for determining the depth of a specific part of the object, may be respectively substituted by the entropy. That is, using the above formula, the entropy $H_1$ is determined for the first patch and the entropy $H_2$ is determined for the second patch (and for each further pair of patches). Then, $H_1$ and $H_2$ are used instead of the $I_1$ and $I_2$ in the formula for determining the depth of a specific part of the object depicted in the first patch and the second patch. That is, the entropy is synonymous for the sharpness.

In the following three optional features for improving the depth estimation accuracy are outlined:

Preferably, the control unit may be configured to monitor adjustments of the focus of at least one of the sensors. For example, the control unit may detect an operation of the focusing means. The focus may be adjusted by a human user and/or by a robot operating the imaging system. That is, if the focus of at least one of the sensors is adjusted the control unit may monitor the amount of adjustment. In other words, the control unit may detect a shift (i.e. a distance) of the focal point of each sensor. Based on the image data, the control unit may detect which part of the image data is sharply depicted (e.g. using edge detection). Further, the control unit may know what distance a sharply depicted portion of the object under examination is from the tip end of the endoscope, for example. By combining the knowledge of the position of the focal point within the image data and which part of the image data is sharply depicted, the control unit may improve the depth estimation. In other words, the control unit may gain information which part of the image data is sharply depicted at present and where the focus point of each sensor lies. As a result, the control unit may determine the depth of the sharply depicted portions of the image data. The monitoring may be conducted in real time. Accordingly, a continuous improvement of the depth estimation is possible. The monitoring of the focus adjustments may e realized by providing an optical encoder, electric measurements and/or other mechanical sensors. By using at least one of the above means the focus adjustments may be efficiently measured. In addition, the measuring accuracy may be increased by using a combination of these measuring means.

Preferably, the control unit may be configured to monitor movements of the imaging system. That is, the spatial position of the imaging system may be monitored by the control unit. For example, if the imaging system is provided in an endoscope, the control unit may detect the spatial position of the endoscope. Preferably, the position is detected in real time. This information may be then used to improve the depth estimation accuracy. The spatial position may be detected by optical trackers, electromagnetic trackers and/or by monitoring actuators. The actuators may be used to operate the imaging system by a robot. That is, if the robot moves the imaging system during operating it, the control unit may detect such movement and may thus determine the current spatial position of the imaging system. Further, the imaging system may include an acceleration senor and/or a rotation sensor. Thus, movements of the imaging system may be accurately monitored. Based on the known spatial position of the imaging system and information which part of the image data is sharply depicted (refer to the above outlined), the depth estimation accuracy may be further improved.

Preferably, the control unit may be configured to infer depth information using a size of known objects within the image data. That is, the control unit may be configured to determine a distance to a known object (e.g. from a tip end of the endoscope) by knowing the dimension of the object. The object may be markings present within the cavity under inspection. In addition, the markings may be provided on instruments additionally used during examination (e.g. during surgery). Further, the object may be an instrument itself or other objects present in the cavity under examination. Accordingly, an optical calibration may be executed in order to improve the depth estimation accuracy.

Improving the depth estimation accuracy may be useful in order to reduce wrong results of the depth estimation. Wrong results may sometimes occur due to the fact that the depth estimation may be based on contrast of portions of the first image data and the second image data (refer to the above outlined). The previously defined three features may be used to check whether the depth estimation is correct or not, for example. The latter feature may be advantageously because there is no additional structural means necessary to execute the optical calibration. In other words, the optical calibration may be implemented by the control unit without the need for any additional sensors etc. However, two or all three of the above features may be executed in order to improve the depth estimation accuracy. Moreover, the information obtained as outlined above may be also used to compensate distortion of the imaging system (e.g. of the endoscope comprising the imaging system). The at least one of the above features may be implemented in using the technique of computer vision. Computer vision may be an interdisciplinary scientific field that deals with how computers can gain high-level understanding from digital images or videos. From the perspective of engineering, it may seek to understand and automate tasks that the human visual system can do. Computer vision tasks may include methods for acquiring, processing, analyzing and understanding digital images, and extraction of high-dimensional data from the real world in order to produce numerical or symbolic information, e.g. in the forms of decisions. Understanding in this context may mean the transformation of visual images (image data) into descriptions of the world that make sense to thought processes and can elicit appropriate action. This image understanding may be seen as the disentangling of symbolic information from image data using models constructed with the aid of geometry, physics, statistics, and learning theory.

Preferably, the optical channel is rotatable such that a field of view of the first sensor and the second sensor is variable. In particular, only the distal end of the optical channel may be configured to be rotated. That is, the optical channel may be rotated only partly. The sensors may be fixed relative to the rotation of the optical channel. Alternatively, the optical device (e.g. a lens or an array of lenses) provided at a distal end of optical channel may be configured to vary the field of view by being rotated. Accordingly, the proximal end of the optical channel may be fixedly held within the imaging system while the distal end may be rotated so as to be directed towards an object to be imaged. The part of the optical channel that may be rotated, may protrude from the imaging system. The optical channel may have an initial position in which the optical channel extends straight without any curvature. In addition, the optical channel may be rotated about the axis of the optical channel in the initial position. Specifically, the optical channel may be configured such that the optical path may be inclined about 20° to 40°, preferably about 30° with respect to the axis of the optical channel in the initial position. Further, the optical paths may have a cone shape once the optical paths have left the optical channel. Said cone may be inclined by rotating at least a part of the optical channel about the central axis. Specifically, by being rotated, the optical paths may be deviated by 30° with respect to the central axis of the optical channel. Further, at least the distal end of the optical channel may be moveable with respect to the sensors. As a result, the imaging system may be used in a plurality of applications even in narrow spaces or cavities. That is, only a part of the optical channel may be directed towards the object to be imaged in order to acquire first and second image data. Accordingly, even objects difficult to access may be imaged by the imaging system. Further, by being able to rotate the field of view about the axis of the optical channel and by being able to incline the field of view with respect to the axis of the optical channel, an all-round view of the cavity under inspection may be provided. For example, an endoscope comprising the imaging system does not need to be moved within the cavity in order to attain an overall impression of the cavity.

Preferably, the first sensor and the second sensor are arranged such that they are inclined in relation to each other. That is, at least two of the sensors are inclined with respect to each other. For example, the sensors are inclined with respect to each other when their photo sensitive surfaces are inclined to each other. The inclination provides the effect that the imaging system may be more compact compared to a configuration in which the sensors a coplanar to each other. Preferably, the sensors are housed in a camera head which is separate from a shaft element configured to be inserted into a cavity under inspection. Accordingly, the camera head may have compact dimensions due to the arrangement of the sensors in an inclined manner. That is, an extension of the camera head along the direction of the shaft may be limited so as to ensure a compact camera head. In particular, the sensors may be inclined by substantially 90° with respect to each other. By substantially 90° may be meant an arrangement of the sensors forming an angle of 90° plus minus 10° between them. Accordingly, the imaging system may be produced efficiently, taking into account an acceptable level of tolerances.

Preferably, the first sensor and the second sensor are configured to use the RGB light spectrum, the green light spectrum and/or the NIR light spectrum to generate the first image data and the second image data. Therefore, depending on the specific application the light spectrum may be used that includes a lot of information under given conditions. Specifically, the green light spectrum has a lot of information under relatively poor light conditions. On the other hand, the NIR light spectrum provides a lot of information in almost dark light conditions. As a result, shapes and information may be easily recognized or determined by the image data under different light conditions. Further, the first sensor and the second sensor may use different light spectrums/channels. For example, the first sensor may use the green spectrum and the second sensor may use the NIR-spectrum. As a result, even under varying light conditions a depth information may be determined.

According to a further aspect of the present invention, a laparoscope comprising the above imaging system is provided. In other words, the laparoscope may be an endoscope including a camera head comprising the above imaging system. The camera head accommodating the imaging system may be connected to the laparoscope via a camera adapter. The focusing ring may be arranged on the camera adapter of the laparoscope so as bridge the camera head and a telescope of the laparoscope. The telescope may be a shaft of the laparoscope. The optical channel may be arranged within the shaft. Further, the shaft may be flexible so as to allow the optical channel to be rotated at a distal end of the laparoscope (e.g. the telescope) or may protrude from the distal end of the laparoscope. Further, the laparoscope may comprise a light source. The light source may be adjustable so as to illuminate an area to which the distal end of the optical channel is directed. Accordingly, the first and second image data may be appropriately generated even in bad light conditions. The light source may be preferably a LED light source. As a result, a laparoscope may be provided that may acquire at least two focus shifted image data using a single camera head. As a result, the laparoscope may have a highly integrated design and may be used in a wide field of applications. The laparoscope may be configured to be operated by a robot. That is, the laparoscope may have an interface configured to receive operation commands from the robot and to transmit information (e.g. image data) to the robot. Accordingly, the laparoscope can be used in an at least partially automated surgical environment.

According to a further aspect of the present invention a method for imaging an object is provided, wherein the method comprising: generating first image data of an object by imaging the object along a first optical path using a first sensor, and generating second image data of the object by imaging the object along a second optical path using a second sensor, wherein the first sensor and the second sensor are focus shifted, and wherein the first optical path and the second optical path are guided at least partly through the same optical channel.

Preferably, the method further comprises the step of dividing the first image data and the second image data into patches, wherein the patches of the first image data and the patches of the second image data correspond to each other. In other words, a patch of the first image data covers exactly the same area as the corresponding patch of the second image data. The corresponding patches of the first image data and of the second image data may be considered as a pair of patches.

Preferably, the method further comprising the step of comparing the first image data and the second image data with each other so as to generate depth information.

Preferably, the images are compared with one another by comparing at least one pair of patches.

Preferably, the first image data and the second image data are generated simultaneously.

The advantages and features described in connection with the device are also applicable to the method and vice versa. Wherever not already described explicitly, individual embodiments or their individual aspects and features can be combined or exchanged with one another without limiting or widening the scope of the described invention, whenever such a combination or exchange is meaningful and in the sense of this invention. Advantages, which are described with respect to one aspect of the present invention are, wherever applicable also advantages of other aspects of the present invention.

Figure 2:
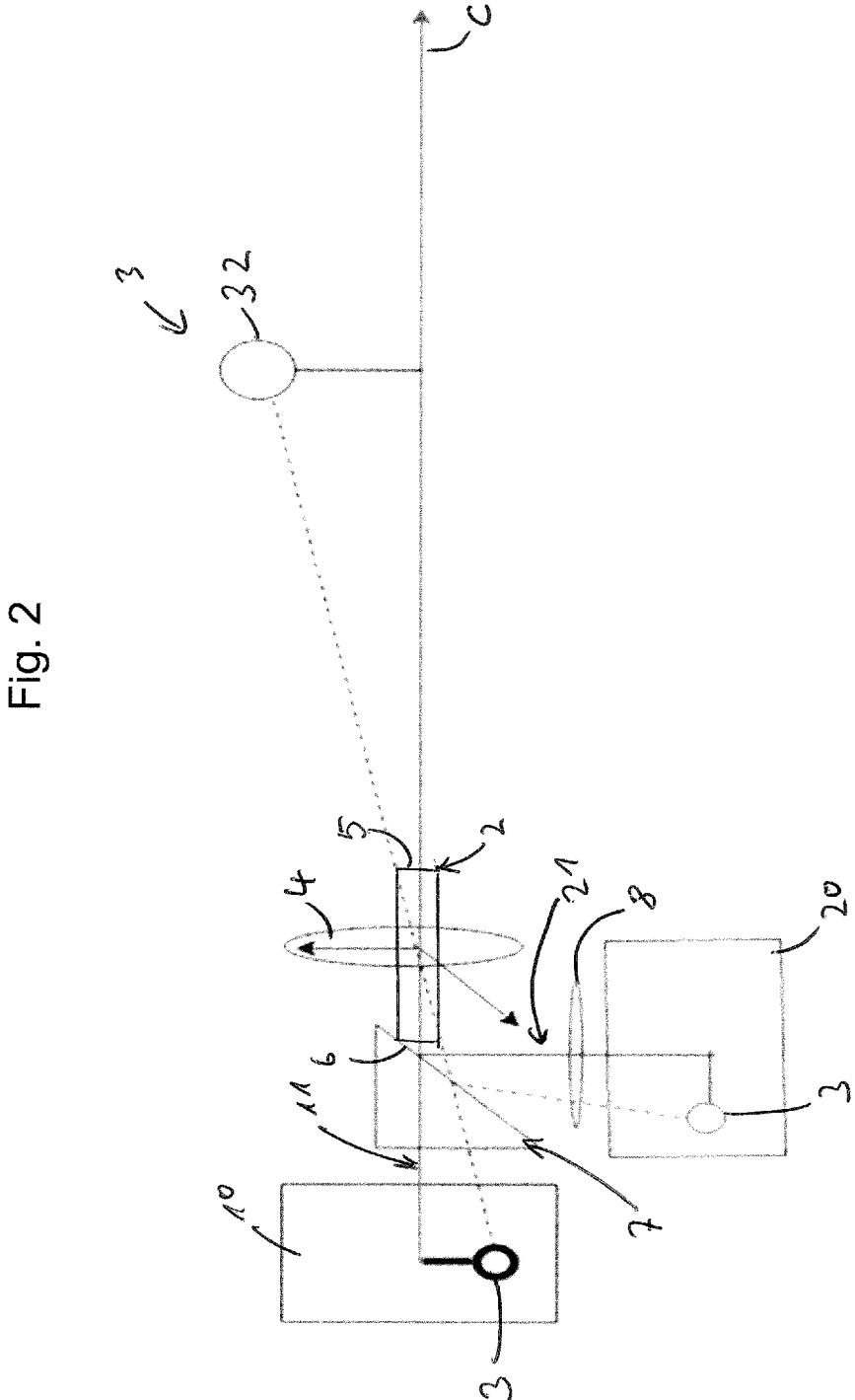
Figure 3:
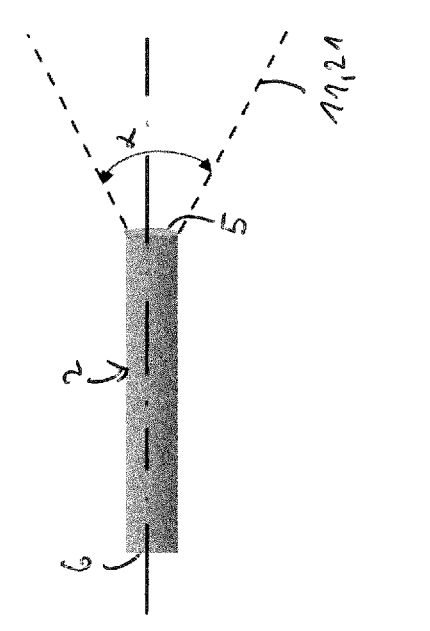
Figure 3:
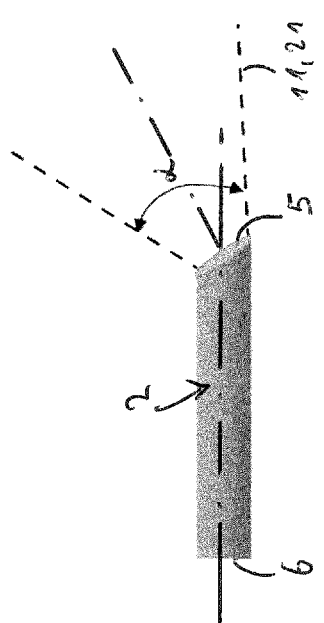
Figure 3:
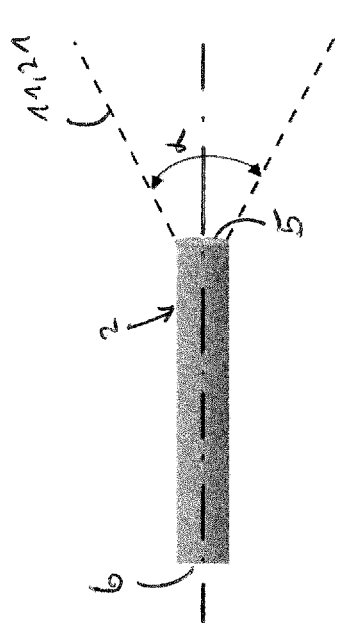
Figure 3:
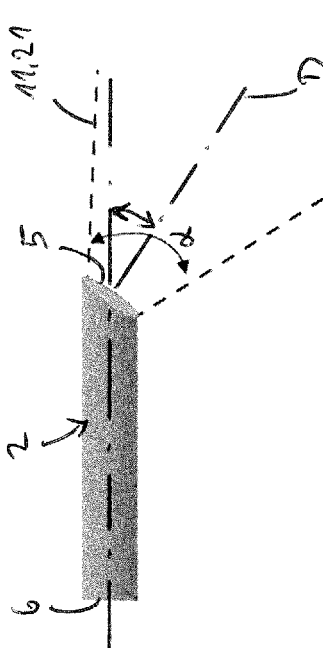
Figure 4:
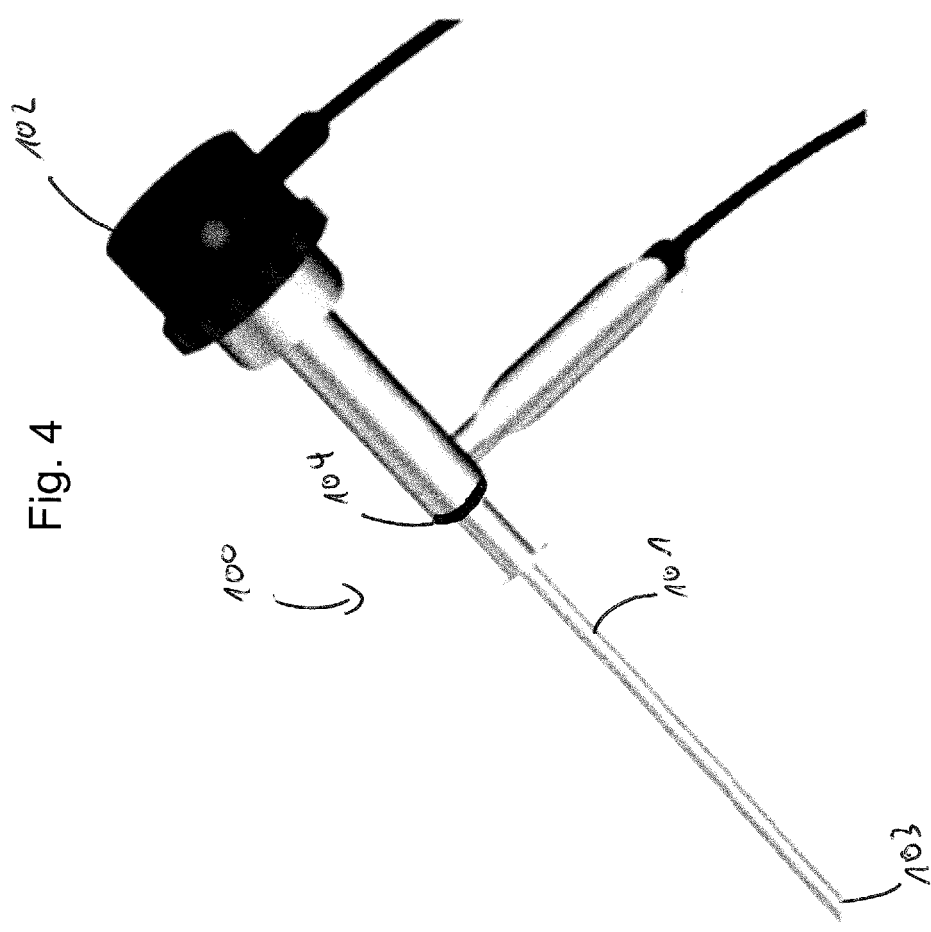

Useful embodiments of the invention shall now be described with reference to the attached figures. Similar elements or features are designated with the same reference signs in the figures. In the figures is:

FIG. 1 a schematic view of an imaging system according to an embodiment of the present invention, FIG. 2 a schematic view of the imaging system according to the embodiment of the present invention, FIG. 3 a schematic view of a part of an imaging system according to an embodiment of the present invention, and FIG. 4 a perspective view of a laparoscope according to an embodiment of the present invention.

FIG. 1 schematically shows an imaging system 1 according to an embodiment of the present invention. In addition, in FIG. 1 there is depicted a coordinate system having an x-axis, a y-axis and a z-axis. The imaging system 1 is configured to image an object 3. The imaging system 1 includes a first sensor 10 and a second sensor 20 configured to generate first image data and second image data. Further, the first sensor 10 and the second sensor 20 are focus shifted. In the present embodiment, both sensors 10, 20 are CMOS sensors. The image data includes spatial information in a x-y-plane (i.e. 2D information). Accordingly, the imaging system 1 includes a first optical path 11 extending between the first sensor 10 and the object 3 and a second optical path 21 extending between the second sensor 20 and the object 3. Further, the imaging system 1 includes an optical channel 2 having a distal end 5 facing the object 3, and a proximal end 6 facing the first sensor 10 and the second sensor 20. The optical channel 2 is an elongated and transparent body extending along its central axis C. In the present embodiment the central axis C extends along the z-axis. The first and second optical paths 11, 21 extend from the first and second sensors 10, 20, respectively, to a beam splitter prism 8 provided within the imaging system 1. At the beam splitter prism 8 the first optical path 11 and the second optical path 21 are merged/split by the beam splitter prism 8 and extend further to the proximal end 6 of the optical channel 2. That is, the beam splitter prism 8 is provided in the optical paths 11, 21 between the sensors 10, 20 and the optical channel 2. Then the first and second optical paths are directed by an optical lens (not depicted in the figures). In another embodiment, each optical path has its own optical lens. Subsequently, the first and second optical paths 11, 21 are both guided through the optical channel 2. From the distal end 5 of the optical channel both optical paths are directed towards the object 3 in the same manner. As a result, the first sensor 10 and the second sensor 20 may image the same portion of the object having the same point of view (i.e. have the same field of view). Moreover, the imaging system 1 includes a focus system 4 configured to adjust the focus (e.g. a focal length) of the first sensor 10 and of the second sensor 20. In the present embodiment, the focus system is a lens arrangement and is provided in the optical channel 2. That is, the focus system 4 is located such that it can adjust the focus of both sensors 10, 20 simultaneously. That is, the optical channel may be made of two portions between which the focus system 4 may be provided. In a further embodiment not depicted in the figures, there is provided a focus system for each sensor such that the focus of each sensor may be individually adjusted. In the present embodiment the focus of the two sensors 10, 20 is set prior to the acquisition of the first and second image data.

Further, the first sensor 10 and the second sensor 20 are arranged within the imaging system 1 such that they are focus shifted. That is, the first sensor 10 has a different focus (i.e. a different focus distance) as compared to the second sensor 20. In other words, the focus point of the first sensor 10 is located at a different position as compared to the focus point of the second sensor 20. In the present embodiment the shifted focus is realized by providing an additional lens 8 in the second optical path 21. That is, the additional lens 8 is provided in addition to an optical system (not depicted in the figures) which may be used to guide the first optical path and the second optical path. Consequently, a same portion of the object 3 cannot be imaged in a sharp manner on both the first sensor 10 and the second sensor 20. In the embodiment depicted in FIG. 1, a first portion 31 of the object 3 is imaged by the first sensor 10 in a sharp manner whereas the first portion 31 imaged by the second sensor 20 is blurred (i.e. is not depicted in a sharp manner).

FIG. 2 schematically shows the imaging system 1 according to the embodiment of the present invention. The imaging system 1 depicted in FIG. 2 is the same as that depicted in FIG. 1. The difference with respect to FIG. 1 is that a second portion 32 of the object 3, located at a different position along the z-axis is depicted. Further, the second portion 32 is imaged by the second sensor 20 in a sharp manner, whereas the second portion 32 is imaged by the first sensor 10 in a blurred manner. Please note that the first portion 31 and second portion 32 depicted in the figures are portions of the object 3 which is omitted in the figures for simplification of the explanation. That is, a portion of the object 3 to be imaged is sharp on the first sensor 10 and another portion of the object 3 to be imaged is sharp on the second sensor 20. As a result, a dual sensor optical imaging system is provided in which the image axes (the first optical path 11 and the second optical path 21) of both sensors is at least partly the same, while the sensors are focus shifted. Therefore, image data may be acquired that is registered perfectly. However, according to a further embodiment that is not depicted in the figures, the imaging system includes more than two sensors each configured and arranged in the similar way as the two sensors of the above embodiment.

Further, the imaging system 1 includes a control unit configured to divide the first image data and the second image data in a plurality of patches. In the present embodiment each patch has a size of 20×20 pixels. In addition, the control unit determines the image information (i.e. the entropy) of each patch. That is, the first image data is divided in the same patches as the second image data. As a result, a pair of patches may be determined. The pair of patches may be composed of a first patch of the first image data and a corresponding second patch of the second image data. The entropy of each patch and the known focus distance of the first sensor 10 and the second sensor 20 is then used to determine the depth (i.e. z-coordinate) of the respective pair of patches. This is done for each pair of patches.

In some embodiments, the focus system 4 is operated so as to shift the focus points of the sensors 10, 20 in a predetermined increment. In some embodiments the focus system 4 is automatically controlled and operated by the control unit. In another embodiment, the focus system 4 may be manually operated by a user via a focusing means (e.g. a focus ring) 104 (see FIG. 3). At each increment, image data are generated by the first sensor 10 and the second sensor 20. The image data may be generated simultaneously or successively by the first sensor 10 and by the second sensor 20. In the present embodiment the control unit determine the depth of each pair of patches using the following formula:

$$d = \frac{(d_1 * I_1 + d_2 * I_2)}{(I_1 + I_2)}$$

wherein
  d is the unknown distance (i.e. depth or z-coordinate) of
    a part of the object depicted in the first patch and the
    second patch,
  $d_1$ is the focus distance of the first sensor,
  $I_1$ is the sharpness of the first patch,
  $d_2$ is the focus distance of the second sensor,
  $I_2$ is the sharpness of the second patch.
  It is to be noted that a careful selection of focusing distances of the first sensor 10 and the second sensor 20 and the patch size selection is needed for the algorithm to work, so these factors should be carefully selected depending on specific configurations of the object to be imaged. The focus distance for each sensor 10, 20 is known. Therefore, the depth information for each patch may be determined using the above formula.

In FIG. 3 a part of an imaging system 1 according to an embodiment of the present invention is depicted. Specifically, in FIG. 3 two pairs of schematic diagrams are depicted. In each diagram, the optical channel 2 is depicted in a schematical manner. Further, the first and second optical paths 11, 21 are schematically depicted (i.e. the first optical path 11 and the second optical path 21 overlap). The optical paths extend from the distal end 6 of the optical channel having a cone shape (i.e. run in a divergence manner). In the present embodiment the cone shape has an acute angle α of 60°. Accordingly, the optical channel 2 in this embodiment includes a lens at its distal end that is configured to divergence the first optical path 11 and the second optical path 21 so as to have and divergence angle of 60°.

In the first row of diagrams, the optical channel 2 is depicted in an initial position. In the second row of diagrams, the optical channel is at least partly rotated so as die direct the optical paths 11, 21 in different directions. In particular, according to the present embodiment the optical channel 2 is at least partly rotatable about the z-axis. Accordingly, the first and second optical paths 11, 21 may be rotated about the z-axis. In the present embodiment the optical paths are inclined such that a central axis D of the optical paths has an angle of 30° to the z-axis (see second row of diagrams in FIG. 3). The diagram on the left side in the second row shows the optical paths 11, 21 redirected to a lower side of the optical path 2. On the other hand, the diagram on the right side in the second row shows the optical paths 11, 21 redirected to an upper side of the optical path 2. That is, the optical paths 11, 21 may be rotated all around the z-axis.

In FIG. 4 a laparoscope 100 according to an embodiment of the present invention is depicted. The laparoscope 100 includes the imaging system 1 within a housing 102. The laparoscope has a shaft 101 having a distal end 103. The optical channel 2 is provided within the shaft 101 of the laparoscope 100. Further, the laparoscope 100 includes a light source (not depicted in the figures) that is configured to emit light from the distal end 103 of the laparoscope along the first optical path 11 and the second optical path 12 towards the object 3.

The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

REFERENCE SIGNS

1 imaging system
2 optical channel
3 object
4 focus system
5 distal end of the optical channel
6 proximal end of the optical channel
7 beam splitter prism
8 lens
10 first sensor
11 first optical path
20 second sensor
21 second optical path
31 first portion of the object
32 second portion of the object
100 laparoscope

101 shaft
102 housing
103 distal end of the laparoscope
104 focusing means
α angle of the optical paths
C axis of the optical channel
D axis of the optical path
x x-axis
y y-axis
z z-axis

The invention claimed is:

1. An imaging system, comprising:
an optical channel configured to transfer light,
a first sensor configured to generate first image data by imaging an object along a first optical path, and
a second sensor configured to generate second image data by imaging the object along a second optical path,
wherein the first sensor and the second sensor are focus shifted, wherein the first optical path and the second optical path are guided at least partly through the optical channel,
wherein the first sensor and the second sensor are arranged such that they are inclined in relation to each other, and
wherein the imaging system further includes a control unit configured to generate depth information of the object based on the first image data and the second image data.

2. The imaging system of claim 1, wherein the first optical path and the second optical path have different lengths.

3. The imaging system of claim 1, wherein the first sensor and the second sensor are further configured to image the object simultaneously.

4. The imaging system of claim 1, further comprising a focus system arranged in the first optical path and/or the second optical path and configured to vary the focus of the first sensor and/or the second sensor.

5. The imaging system of claim 4, wherein the system further comprises a sensor focusing element configured to control the focus system such that the focus of the first sensor and/or the second sensor may be adjusted.

6. The imaging system of claim 1, wherein the first image data and the second image data represent an identical area of the object.

7. The imaging system of claim 1, wherein the control unit is further configured to generate the depth information by comparing the entropy of at least one first patch of the first image data and of at least one second patch of the second image data, wherein the location of the at least one first patch in the first image data corresponds to the location of the at least one second patch in the sec-ond image data.

8. The imaging system of claim 7, wherein the at least one first patch has the same size as the at least one second patch.

9. The imaging system of claim 8, wherein the at least one first patch is a size of 20×20 pixels.

10. The imaging system of claim 8, wherein the at least one second patch is a size of 20×20 pixels.

11. The imaging system of claim 1, wherein the optical channel is rotatable such that a field of view of the first sensor and the second sensor is variable.

12. A laparoscope comprising the imaging system of claim 1.

13. A method for imaging an object, the method comprising:
generating first image data of an object by imaging the object along a first optical path using a first sensor, and generating second image data of the object by imaging the object along a second optical path using a second sensor, wherein the first sensor and the second sensor are focus shifted, wherein the first optical path and the second optical path are guided at least partly through the same optical channel, wherein the first sensor and the second sensor are arranged such that they are inclined in relation to each other, and wherein the first image data and the second image data are compared with each other to generate depth information.

14. The method of claim 13, wherein the first image data and the second image data are generated simultaneously.

\* \* \* \* \*